(12) United States Patent
Shin et al.

(10) Patent No.: US 9,183,760 B2
(45) Date of Patent: Nov. 10, 2015

(54) METHOD AND APPARATUS FOR RECOGNIZING SIGN LANGUAGE USING ELECTROMYOGRAM SENSOR AND GYRO SENSOR

(75) Inventors: Hyun Chool Shin, Seoul (KR); Kyung Jin You, Seoul (KR); Ki Won Rhee, Seoul (KR); Hee Su Kang, Seoul (KR)

(73) Assignee: Foundation of Soongsil University-Industry Cooperation, Seoul (KR)

( * ) Notice: Subject to any disclaimer, the term of this patent is extended or adjusted under 35 U.S.C. 154(b) by 229 days.

(21) Appl. No.: 13/979,337

(22) PCT Filed: Oct. 28, 2011

(86) PCT No.: PCT/KR2011/008136
§ 371 (c)(1),
(2), (4) Date: Jul. 11, 2013

(87) PCT Pub. No.: WO2012/077909
PCT Pub. Date: Jun. 14, 2012

(65) Prior Publication Data
US 2013/0295529 A1 Nov. 7, 2013

(30) Foreign Application Priority Data
Dec. 10, 2010 (KR) .......................... 10-2010-0126191

(51) Int. Cl.
*G09B 21/00* (2006.01)
*G06F 3/01* (2006.01)
(Continued)

(52) U.S. Cl.
CPC .............. *G09B 21/009* (2013.01); *G06F 3/017* (2013.01); *G06F 3/038* (2013.01); *G06F 3/0346* (2013.01);
(Continued)

(58) Field of Classification Search
CPC ........................................................ G09B 21/00
USPC ........................................................ 434/112
See application file for complete search history.

(56) References Cited

U.S. PATENT DOCUMENTS

| 5,917,912 A | 6/1999 | Ginter et al. |
| 2008/0059448 A1 | 3/2008 | Chang et al. |

(Continued)

FOREIGN PATENT DOCUMENTS

| JP | 11296425 A | 10/1999 |
| KR | 1020050052555 A | 6/2005 |

(Continued)

OTHER PUBLICATIONS

Kosmidou, Vasiliki E. 'Sign Language Recognition Using Intrinsic-Mode Sample Entropy on sEMG and Accelerometer Data'. IEEE Transactions on Biomedical Engineering, vol. 56, No. 12, Dec. 2009. [retrieved on Mar. 19, 2015]. Retrieved from the Internet: http://ieeexplore.ieee.org/stamp/stamp.jsp?arnumber=4760276, as applied to claims 1 and 6 above, an.*

(Continued)

*Primary Examiner* — Xuan Thai
*Assistant Examiner* — Robert P Bullington
(74) *Attorney, Agent, or Firm* — Novick, Kim & Lee, PLLC; Sang Ho Lee (57) ABSTRACT

Provided are a method and apparatus for recognizing sign language using an electromyogram sensor and a gyro sensor. The method includes the steps of (a) receiving a gyro measurement signal and an electromyogram measurement signal from the gyro sensor and the electromyogram sensor which are attached to the body of a subject, (b) determining to which of groups clustered with similar fingerspelling motions the gyro measurement signal belongs, (c) acquiring a Gaussian model for the electromyogram measurement signal, and (d) comparing the acquired Gaussian model with Gaussian candidate models for candidate fingerspelling motions which belong to the group determined in step (b), and recognizing the candidate fingerspelling motion corresponding to the Gaussian candidate model that is most similar to the acquired Gaussian model as the fingerspelling motion of the subject.

14 Claims, 10 Drawing Sheets

(51) Int. Cl.
*G06F 3/038* (2013.01)
*G06K 9/00* (2006.01)
*G06F 3/0346* (2013.01)
*A61B 5/0488* (2006.01)
*A61B 5/11* (2006.01)
*A61B 5/00* (2006.01)

(52) U.S. Cl.
CPC ........ *G06K 9/00355* (2013.01); *G06K 9/00536* (2013.01); *A61B 5/0488* (2013.01); *A61B 5/1114* (2013.01); *A61B 5/1125* (2013.01); *A61B 5/6825* (2013.01); *A61B 2562/0219* (2013.01)

(56) References Cited

U.S. PATENT DOCUMENTS

2008/0066185 A1    3/2008    Lester et al.
2010/0095121 A1    4/2010    Shetty et al.

FOREIGN PATENT DOCUMENTS

KR    1020080028084 A    3/2008
KR    1020100047793 A    5/2010
KR    1020100121871 A    11/2010
WO       2008154428 A1    12/2008

OTHER PUBLICATIONS

Li, Yun, et al., 'Automatic Recognition of Sign Language Subwords based on Portable Accelerometer and EMG Sensors'. ICMI-MLMI'10, Nov. 8-10, 2010, Beijing, China. Copyright 2010 ACM 978-1-4503-0414—Jun. 10, 2011. [retrieved on Mar. 19, 2015]. Retrieved from the Internet: http://dl.acm.org/citation.cfm?id=1891926.*

* cited by examiner

CLUSTERING RESULT

GROUP1

FIVE CONSONANT MODELS:
EIGHT-AVERAGE SUCCESS RATE:
80

| PERFORMING MOTION | ㄱ | ㅅ | ㅈ | ㅊ | ㅋ |
|---|---|---|---|---|---|
| ㅋ |  | 2 | 7.5 |  | 90.5 |
| ㅊ | 7 | 2 | 5 | 85 | 1 |
| ㅈ | 4 | 26 | 59 | 3.5 | 7.5 |
| ㅅ | 1 | 75 | 19.5 | 2.5 | 2 |
| ㄱ | 90.5 | 0.5 | 7 | 2 |  |

DISCRIMINATING MOTION

GROUP2

FIVE CONSONANT MODELS:
EIGHT-AVERAGE SUCCESS RATE:
88.4

| PERFORMING MOTION | ㄴ | ㄷ | ㄹ | ㅌ | ㅎ |
|---|---|---|---|---|---|
| ㅎ | 1 |  | 1 |  | 98 |
| ㅌ |  | 1.5 | 9 | 89.5 |  |
| ㄹ | 2 | 9.5 | 78.5 | 8 | 2 |
| ㄷ | 1.5 | 87.5 | 11 |  |  |
| ㄴ | 88.5 | 1 | 9 |  | 1.5 |

DISCRIMINATING MOTION

GROUP3

FOUR CONSONANT MODELS:
EIGHT-AVERAGE SUCCESS RATE:
95.375

| PERFORMING MOTION | ㅁ | ㅂ | ㅇ | ㅍ |
|---|---|---|---|---|
| ㅍ |  | 8 |  | 92 |
| ㅇ |  |  | 99 | 1 |
| ㅂ | 1 | 93.5 |  | 5.5 |
| ㅁ | 97 | 2.6 |  | 0.5 |

DISCRIMINATING MOTION

FOURTEEN CONSONANT MODELS:
NINE-AVERAGE SUCCESS RATE: 85.5%

| PERFORMING MOTION | ㄱ | ㄴ | ㄷ | ㄹ | ㅁ | ㅂ | ㅅ | ㅇ | ㅈ | ㅊ | ㅋ | ㅌ | ㅍ | ㅎ |
|---|---|---|---|---|---|---|---|---|---|---|---|---|---|---|
| ㅎ |  |  |  |  |  |  | 18 |  |  |  |  |  |  | 82 |
| ㅍ |  |  |  | 13 |  |  |  |  |  |  |  |  | 87 |  |
| ㅌ |  | 1 | 4 |  |  | 1 |  |  | 1 |  |  | 93 |  |  |
| ㅋ |  |  |  |  |  | 1 |  | 5 | 1 | 92 | 1 |  |  |  |
| ㅊ | 8 |  |  |  |  | 1 |  | 8 | 81 | 1 | 1 |  |  |  |
| ㅈ | 2 |  | 3 |  |  |  | 26 |  | 61 | 1 | 7 |  |  |  |
| ㅇ |  |  |  |  |  |  | 86 |  |  |  |  |  |  | 14 |
| ㅅ |  | 9 | 1 |  |  | 74 |  | 15 |  | 1 |  |  |  |  |
| ㅂ |  |  |  |  | 99 |  |  |  |  |  | 1 |  |  |  |
| ㅁ |  |  |  | 100 |  |  |  |  |  |  |  |  |  |  |
| ㄹ |  | 1 | 3 | 84 |  |  |  |  |  |  |  | 10 |  | 2 |
| ㄷ | 2 |  | 87 | 10 |  |  |  |  | 1 |  |  |  |  |  |
| ㄴ |  | 90 | 1 | 9 |  |  |  |  |  |  |  |  |  |  |
| ㄱ | 81 | 4 | 4 | 2 |  | 1 |  | 7 | 1 |  |  |  |  |  |

DISCRIMINATING MOTION  UNIT: %

FOURTEEN VOWEL MODELS:
NINE-AVERAGE SUCCESS RATE: 75.1429%

| PERFORMING MOTION | ㅏ | ㅑ | ㅓ | ㅕ | ㅗ | ㅛ | ㅜ | ㅠ | ㅡ | ㅊ | ㅣ | ㅐ | ㅔ | ㅖ |
|---|---|---|---|---|---|---|---|---|---|---|---|---|---|---|
| ㅖ |  |  | 3 |  | 5 |  | 6 | 8 | 3 |  |  |  | 6 | 69 |
| ㅔ |  |  | 12 |  |  |  | 1 |  |  |  |  |  | 81 | 6 |
| ㅐ |  |  |  | 1 |  |  |  | 3 |  | 1 | 7 | 87 |  | 1 |
| ㅒ | 4 |  |  |  |  |  |  |  |  | 15 | 67 | 14 |  |  |
| ㅣ |  |  | 1 |  | 5 |  |  |  |  | 75 | 19 |  |  |  |
| ㅡ |  | 1 | 10 | 11 | 3 | 2 | 1 |  | 71 | 1 |  |  |  |  |
| ㅠ |  |  |  | 1 |  | 16 | 86 | 2 |  |  |  |  |  | 1 |
| ㅜ |  |  |  | 4 |  | 1 | 71 | 10 | 3 |  |  |  |  | 11 |
| ㅛ |  |  | 2 | 20 |  | 69 | 1 |  | 3 |  |  |  |  | 5 |
| ㅗ | 9 |  | 1 |  | 82 |  |  |  | 1 | 7 |  |  |  |  |
| ㅕ |  |  | 4 | 75 |  | 8 | 4 |  | 6 |  |  |  |  | 3 |
| ㅓ | 5 |  | 50 | 7 | 3 |  |  |  | 18 |  |  |  | 16 | 1 |
| ㅑ |  | 86 |  | 4 |  | 1 |  | 1 |  | 2 | 5 | 1 |  |  |
| ㅏ | 89 |  | 1 |  | 3 |  |  |  |  | 4 | 3 |  |  |  |

DISCRIMINATING MOTION  UNIT: %

METHOD AND APPARATUS FOR RECOGNIZING SIGN LANGUAGE USING ELECTROMYOGRAM SENSOR AND GYRO SENSOR

TECHNICAL FIELD

The present invention relates to a method and apparatus for recognizing sign language using an electromyogram sensor and a gyro sensor, and more particularly, to a method and apparatus for recognizing sign language using an electromyogram sensor and a gyro sensor, both of which are attached to a part of the body of a subject.

BACKGROUND ART

Fingerspelling refers to a method of indicating each letter of a Korean alphabet (Hangul) or each number with fingers. Dactylological devices that are known at present photograph and analyze fingerspelling motions. This method requires complicated image processing and a resultant expensive image processing apparatus. This image processing apparatus requires a long image processing time, has difficulty in immediately recognizing the fingerspelling motions, and is inconvenient to carry.

DISCLOSURE

Technical Problem

Accordingly, the present invention is directed to a method and apparatus for recognizing sign language using an electromyogram sensor and a gyro sensor, both of which are attached to a part of the body of a subject, which are capable of easily recognizing fingerspelling motions of the subject using signals of the electromyogram sensor and the gyro sensor.

Technical Solution

According to an aspect of the present invention, there is provided a method for recognizing sign language using an electromyogram sensor and a gyro sensor. The method includes the steps of (a) receiving a gyro measurement signal and an electromyogram measurement signal from the gyro sensor and the electromyogram sensor which are attached to the body of a subject, (b) determining to which of groups clustered with similar fingerspelling motions the gyro measurement signal belongs, (c) acquiring a Gaussian model for the electromyogram measurement signal, and (d) comparing the acquired Gaussian model with Gaussian candidate models for candidate fingerspelling motions which belong to the group determined in step (b), and recognizing the candidate fingerspelling motion corresponding to the Gaussian candidate model that is most similar to the acquired Gaussian model as the fingerspelling motion of the subject.

According to another aspect of the present invention, there is provided an apparatus for recognizing sign language using an electromyogram sensor and a gyro sensor. The apparatus includes a signal receiving part receiving a gyro measurement signal and an electromyogram measurement signal from the gyro sensor and the electromyogram sensor which are attached to the body of a subject, a group determining part determining to which of groups clustered with similar fingerspelling motions the gyro measurement signal belongs, a model acquiring part acquiring a Gaussian model for the electromyogram measurement signal, and sign language recognizing part comparing the acquired Gaussian model with Gaussian candidate models for candidate fingerspelling motions which belong to the group determined by the group determining part, and recognizing the candidate fingerspelling motion corresponding to the Gaussian candidate model that is most similar to the acquired Gaussian model as the fingerspelling motion of the subject.

Advantageous Effects

According to the method and apparatus for recognizing sign language using an electromyogram sensor and a gyro sensor in accordance with the present invention, accuracy and reliability of the recognition of fingerspelling motions can be enhanced using clustering data of the similar fingerspelling motions based on the gyro sensor and Gaussian model data of each fingerspelling motion based on the electromyogram sensor.

MODE FOR INVENTION

Hereinafter, exemplary embodiments of a method and apparatus of recognizing sign language using an electromyogram sensor and a gyro sensor in accordance with the present invention will be described in detail with reference to the accompanying drawings.

The present invention relates to a method and apparatus of recognizing sign language using an electromyogram sensor and a gyro sensor and is adapted to be able to increase accuracy and reliability of the recognition of fingerspelling motions using clustering data of similar fingerspelling motions using the gyro sensor and Gaussian model data of each fingerspelling motion using the electromyogram sensor.

Figure 1:
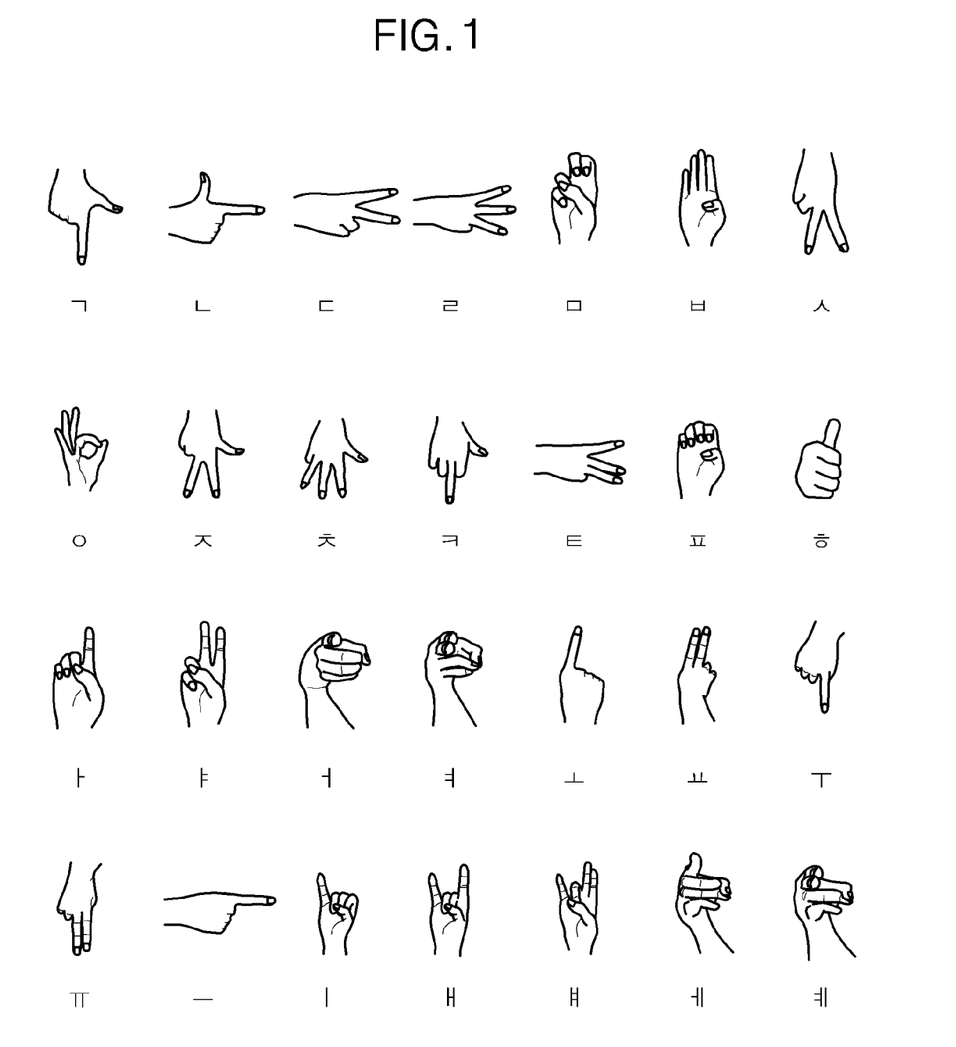
FIG. 1 shows examples of fingerspelling motions for consonants and vowels constituting a Korean alphabet.

FIG. 1 shows examples of fingerspelling motions for consonants and vowels constituting a Korean alphabet. The fingerspelling motions generally use fingers. In case of the Korean alphabet, a total of 28 motions summing up the consonants and vowels are made, and all letters can be expressed by a total of 28 phonemes.

Figure 2:
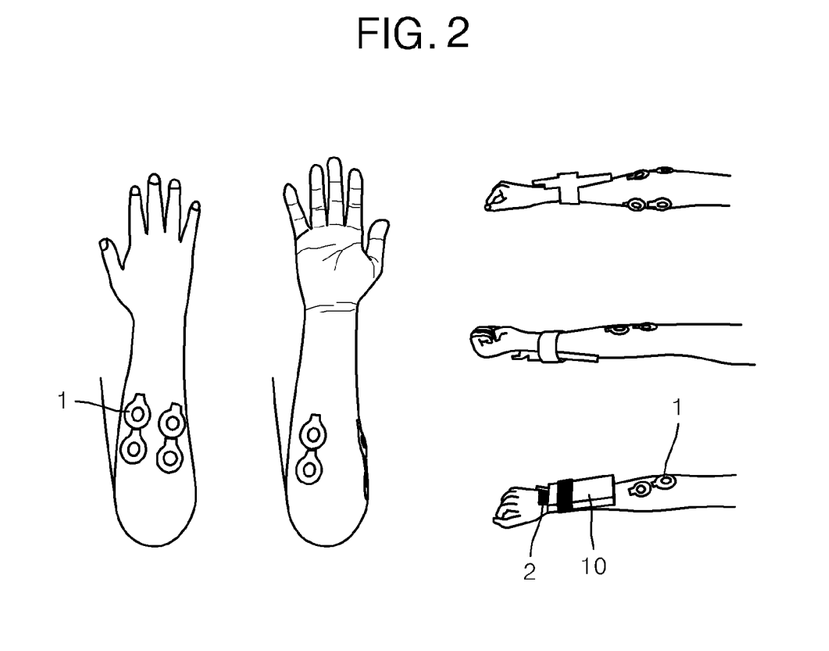
FIG. 2 shows an example in which an electromyogram sensor and a gyro sensor are mounted in accordance with the present invention.

FIG. 2 shows an example in which an electromyogram sensor and a gyro sensor are mounted in accordance with the present invention. The electromyogram sensor and the gyro sensor are attached to a part of the body of a subject. In FIG. 2, the gyro sensor 2 is attached to the vicinity of a wrist, and the electromyogram sensor 1 is attached to the vicinity of a forearm.

Here, a sensor module 10 is a module for measuring Bluetooth-based electromyogram and gyro signals. The electromyogram sensor 1 is connected to a sensor module 10 in a state in which it is attached to the forearm. The gyro sensor 2 is mounted in the sensor module 10. The electromyogram sensor 1 has a total of four channels. In the present embodiment, all of the four channels are used. The present invention is given as an example in which the electromyogram sensor 1 and the gyro sensor 2 are mounted on the vicinities of the forearm and the wrist, but not essentially limited thereto.

Figure 3:
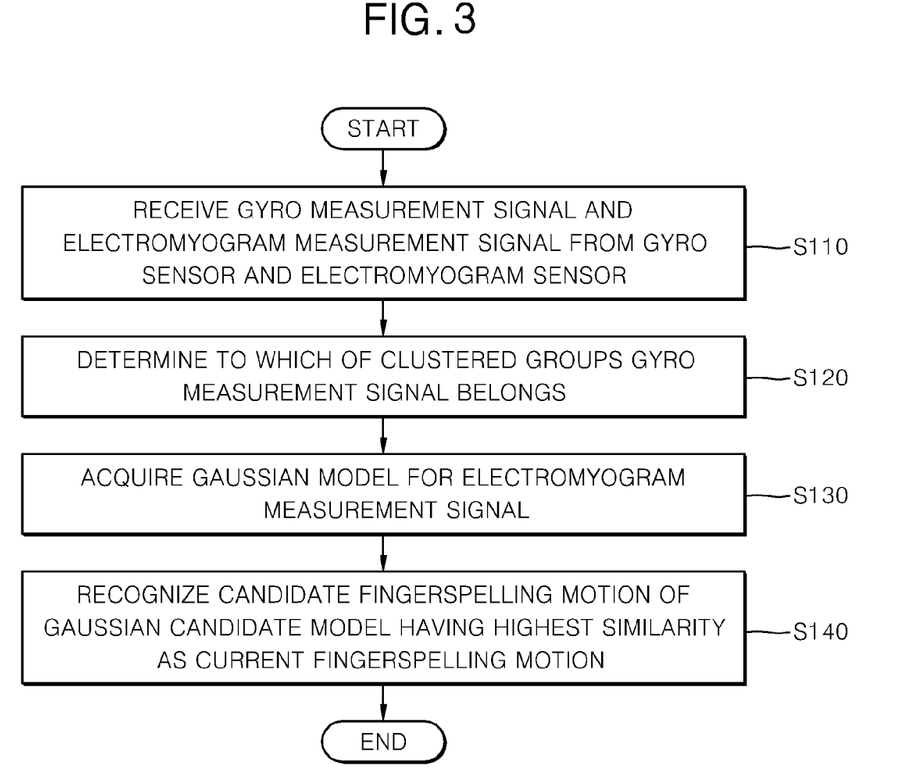
FIG. 3 is a flow chart showing a method of recognizing sign language using an electromyogram sensor and a gyro sensor in accordance with the present invention.
Figure 4:
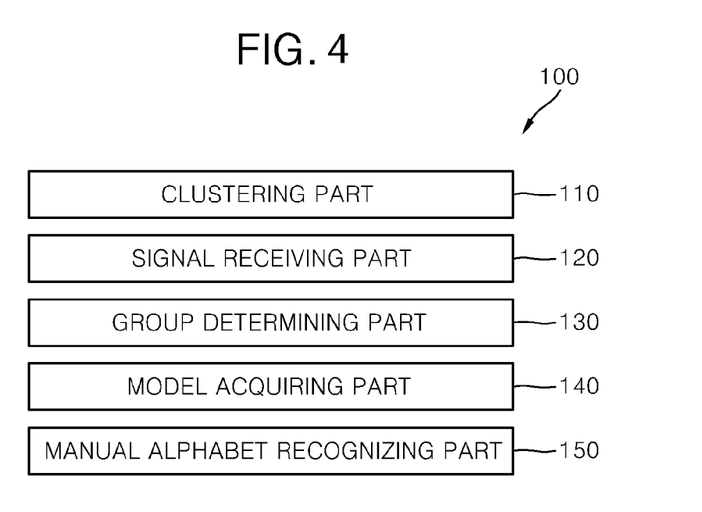
FIG. 4 is a block diagram showing an apparatus for recognizing sign language using an electromyogram sensor and a gyro sensor in accordance with the present invention.

FIG. 3 is a flow chart showing a method of recognizing sign language using an electromyogram sensor and a gyro sensor in accordance with an embodiment of the present invention. FIG. 4 is a constitutional view of an apparatus used for the method of FIG. 3. The apparatus 100 includes a clustering part 110, a signal receiving part 120, a group determining part 130, a model acquiring part 140, and sign language recognizing part 150.

Hereinafter, the method of recognizing sign language using an electromyogram sensor and a gyro sensor will be described in detail with reference to FIGS. 3 and 4.

In the present invention, prior to determining fingerspelling motions, the fingerspelling motions that are similar in characteristic of a signal measured from the gyro sensor 2 are clustered into groups using the clustering part 110.

The gyro sensor 2 is attached to the vicinity of the wrist and uses a bidirectional rotation axis. Thus, angular velocities of pitch and roll rotations are measured according to a quantity of rotation of the wrist in the event of the fingerspelling motion. The measured angular velocities are different according to the fingerspelling motion. The motions that are similar in angular velocity may be clustered into groups. Hereinafter, this will be described in detail.

A roll rotational angle $g_r[n]$ and a pitch rotational angle $g_p[n]$ that are values obtained by integrating an angular velocity $v_r[n]$ of roll rotation and an angular velocity $v_p[n]$ of pitch rotation which are acquired by the gyro sensor 2 over time are defined as Equation 1 below.

$$g_r[n]=\Sigma_{t=1}^{\infty}\int_0^{0.1} V_r[n]dn, \; g_p[n]=\Sigma_{t=1}^{\infty}\int_0^{0.1} V_p[n]dn \quad \text{Equation 1}$$

Here, n indicates a discrete time index. The roll and pitch rotational angles can be expressed by a two-dimensional coordinate value G(t) using the discrete time index. The two-dimensional coordinate value G(t) is given as Equation 2.

$$G(t)=(g_r(t), g_p(t)) \quad \text{Equation 2}$$

Figure 5:
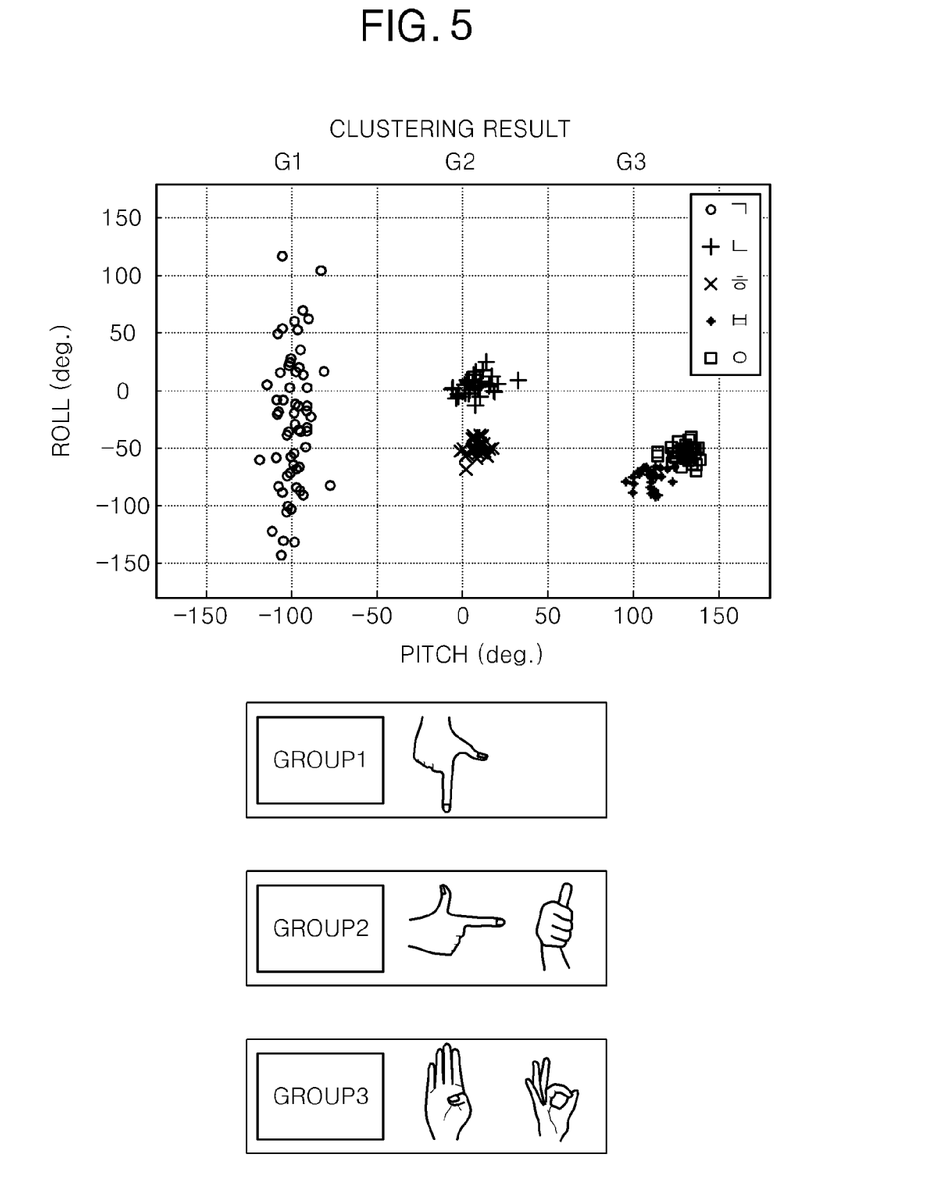
FIG. 5 shows examples of fingerspelling motion groups in a clustering process in accordance with the present invention.

FIG. 5 shows examples of fingerspelling motion groups in a clustering process in accordance with an embodiment of the present invention. A total of three groups are present according to similarity of the motion. Group 1 represents the fingerspelling motions in which the fingers are oriented downward, and Group 2 represents the fingerspelling motions in which the fingers are parallel with the ground. Group 3 represents the fingerspelling motions in which the fingers are oriented upward.

The clustering process will be described below in detail. First, rotational angle coordinate samples of the fingerspelling motions are obtained using roll rotation values and pitch rotation values obtained from the gyro sensor 2 as in Equation 2 (process a).

A distance between the "rotational angle coordinates" of each of the rotational angle coordinate samples of the fingerspelling motions and the "central coordinates set for each group" is measured to allocate the rotational angle coordinates to the corresponding group of the nearest distance (process b). For example, the distance between the rotational angle coordinates of each fingerspelling motion and the central coordinates of each group which are obtained at present is measured. In the case of the three groups, three distances are measured. The rotational angle coordinates are allocated to the group corresponding to the shortest of the three distances. Here, the central coordinates are gradually corrected in the clustering process, and the samples having a similar signal attribute can be gradually congregated into the center. This is made in the following process.

After the process b, an average value of the rotational angle coordinates and the central coordinates is calculated to obtain new central coordinates (process c). Thus, the central coordinates are gradually narrowed so as to be close to the rotational angle coordinate samples.

Afterwards, the process of allocating the rotational angle coordinates (process b) and the process of obtaining the new central coordinates (process c) are repeated for each rotational angle coordinate sample. Thereby, the rotational angle coordinates of the samples are congregated according to each group and finally clustered.

Figure 6:
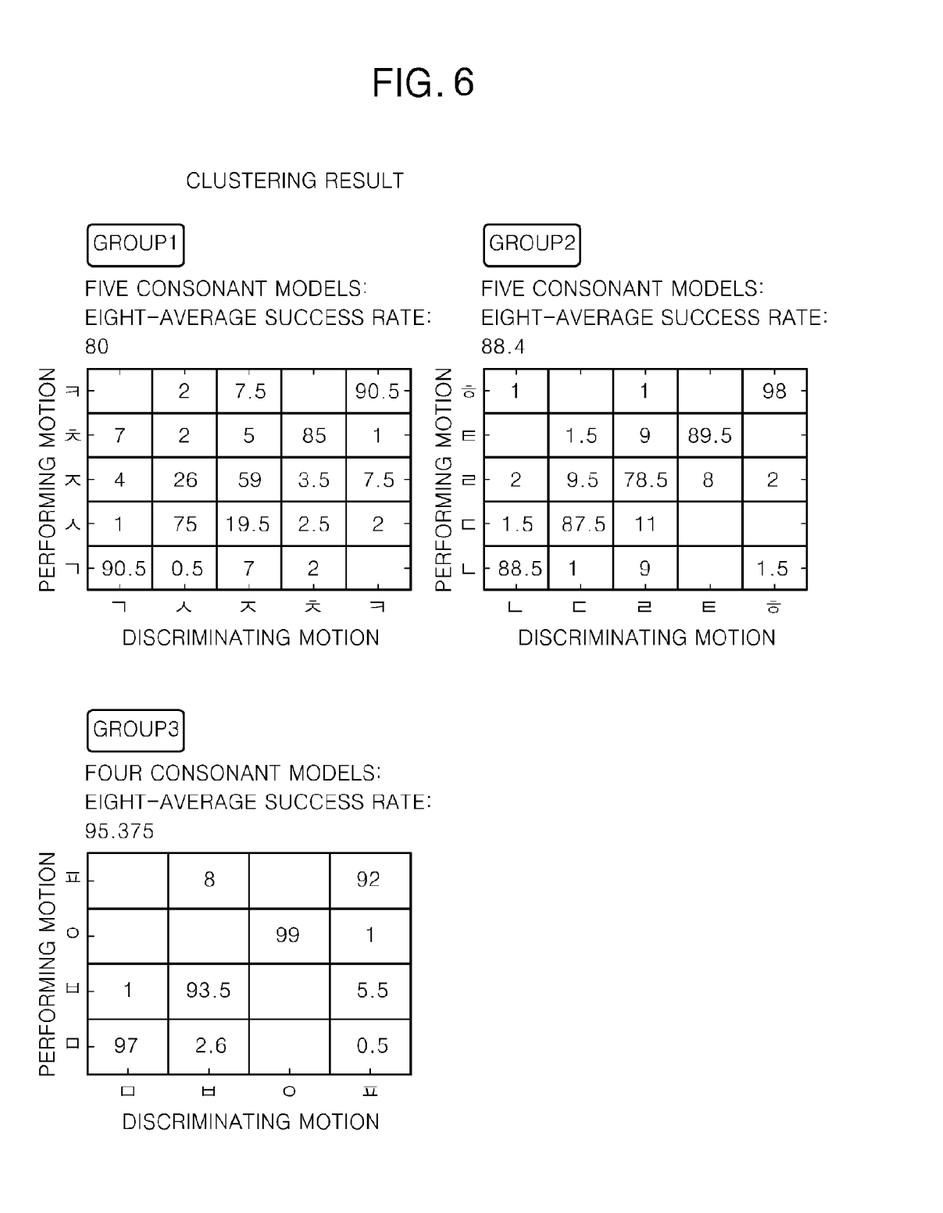
FIG. 6 shows a result recognized by the gyro sensor in a clustering process in accordance with the present invention.

FIG. 6 shows a result recognized by the gyro sensor in a clustering process in accordance with an embodiment of the present invention. The success rates of Groups 1, 2, and 3 are 80%, 88.4%, and 95.4%, and an average success rate thereof is about 87.9% and is very high. It can be found that the result is reliable.

The clustering process is not limited to the foregoing. More various modifications may be present based on information that can be measured by the gyro sensor. For example, the clustering may be performed using a tridirectional rotation axis.

Hereinafter, a process of recognizing the fingerspelling motions of the subject will be described in detail.

First, the signal receiving part 110 receives a gyro measurement signal and an electromyogram measurement signal from the gyro sensor 2 and the electromyogram sensor 1 attached to the part of the body of the subject, i.e., the wrist and the forearm (S110).

Next, the group determining part 130 determines to which group the group of the gyro measurement signal received in step S110 among the groups in which the similar fingerspelling motions as described above are clustered in advance belongs (S120). That is, the coordinates according to roll and pitch rotational angles of the received gyro measurement signal are obtained through Equations 1 and 2, and then it is determined to which of the three groups the obtained coordinates belong.

Afterwards, a Gaussian model of the electromyogram measurement signal is acquired by the model acquiring part 140 (S130). In the case of the present embodiment, four electromyogram sensors 1 of four channels are used. Thus, in step S130, an entrophy of the electromyogram measurement signal of each of the four electromyogram sensors 1 is obtained, and the Gaussian model according to the entropy is acquired.

Figure 7:
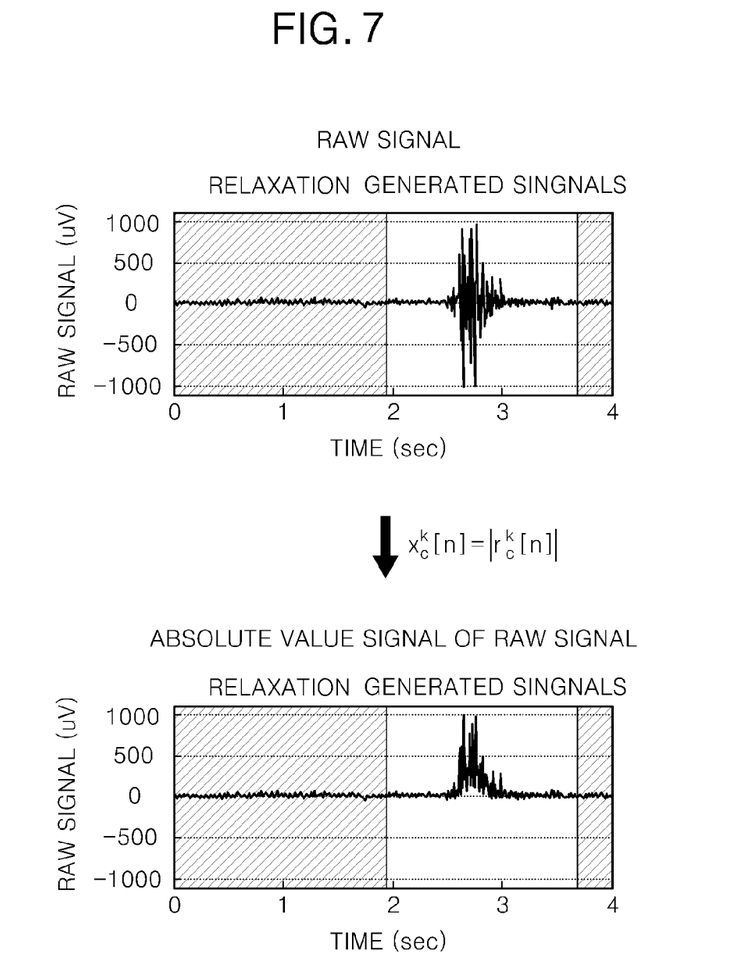
FIG. 7 shows an example of converting a raw signal of the electromyogram sensor into an absolute value signal in accordance with the present invention.

The process of acquiring the Gaussian model will be described below in detail. FIG. 7 shows an example of converting a raw signal of the electromyogram sensor into an absolute value signal in accordance with the present invention.

The process of FIG. 7 is expressed by Equation 3.

$$x_c^k = |r_c^k[n]| \quad \text{Equation 3}$$

Here, $r_c^k[n]$ is the raw signal, and $x_c^k[n]$ is the signal taking an absolute value of the raw signal. In Equation 3, k means an arbitrary fingerspelling motion, and c means the channels (one to four channels) of the electromyogram sensors 1. In the case of the Korean alphabet (Hangul), k ranges from 1 to 28. "n" indicates the discrete time index. Equation 3 means the value taking the absolute value of the electromyogram raw signal generated from the electromyogram sensor 1 of a c-th channel when the arbitrary fingerspelling motion k is performed. The process of taking the absolute value facilitates the following process of analyzing the signal.

Figure 8:
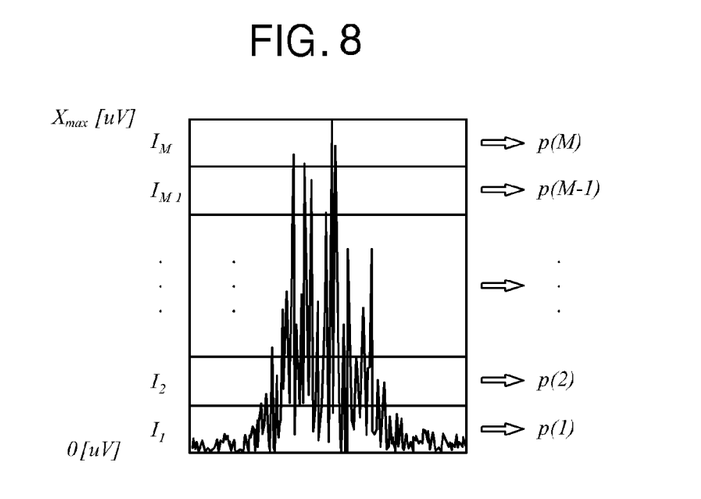
FIG. 8 shows an example of dividing the converted signal of FIG. 7 into sections in order to obtain an entropy of the converted signal.

To obtain the entropy using the signal converted by Equation 3, section-specific probabilities of the converted signal should be obtained. FIG. 8 shows an example of dividing the converted signal of FIG. 7 into sections in order to obtain an entropy of the converted signal. The transverse axis of FIG. 8 indicates a time, and the longitudinal axis indicates an intensity of the signal.

Referring to FIG. 8, first, when the intensity (unit: uV) of the electromyogram signal is uniformly divided into an M number from 0 to $x_{Max}$, a total of m (=1 to M) sections are generated, and names thereof are designated as $I_1$ to $I_M$. That is, a range of the electromyogram signal is a value between 0 and $x_{Max}$, and a value of $x_{Max}$ may be set at a signal receiving device of the electromyogram sensor.

A content of FIG. 8 can be summarized by Equation 4.

$$p(x_m) = Pr(X = x_m), \ 0 \le p(x_m) \le 1 \quad \text{Equation 4}$$

$$\Sigma_{m=1}^M p(x_m) = 1$$

Equation 4 indicates a general probability theory, and detailed description will be omitted.

Here, a probability $p_c^k(m)$ of a value dividing the number of samples of a signal belonging within each section $I_M$ by the number of total samples of the signals is expressed as Equation 5.

That is, $p_c^k(m)$ indicates a probability at which the signal sample is present in the section $I_M$.

$$P_c^k(m) = \frac{\text{number of samples} \in I_m}{\text{number of total samples}}, \quad \text{Equation 5}$$

$$I_m = \left\{ x_c^k[\cdot] \middle| \frac{(m-1)}{M} x_{max} \le x_c^k[\cdot] < \frac{m}{M} x_{max} \right\}$$

On the basis of this, the entropy of the electromyogram measurement signal is calculated by Equation 6.

$$H(X) = -\Sigma_{m=1}^M p(x_m) \log p(x_m) \quad \text{Equation 6}$$

The entropy of the signal X is calculated by Equation 6, and the value of Equation 5 is used. The entropies of the electromyogram measurement signals of the four electromyogram sensors 1 are obtained by Equation 6.

Figure 9:
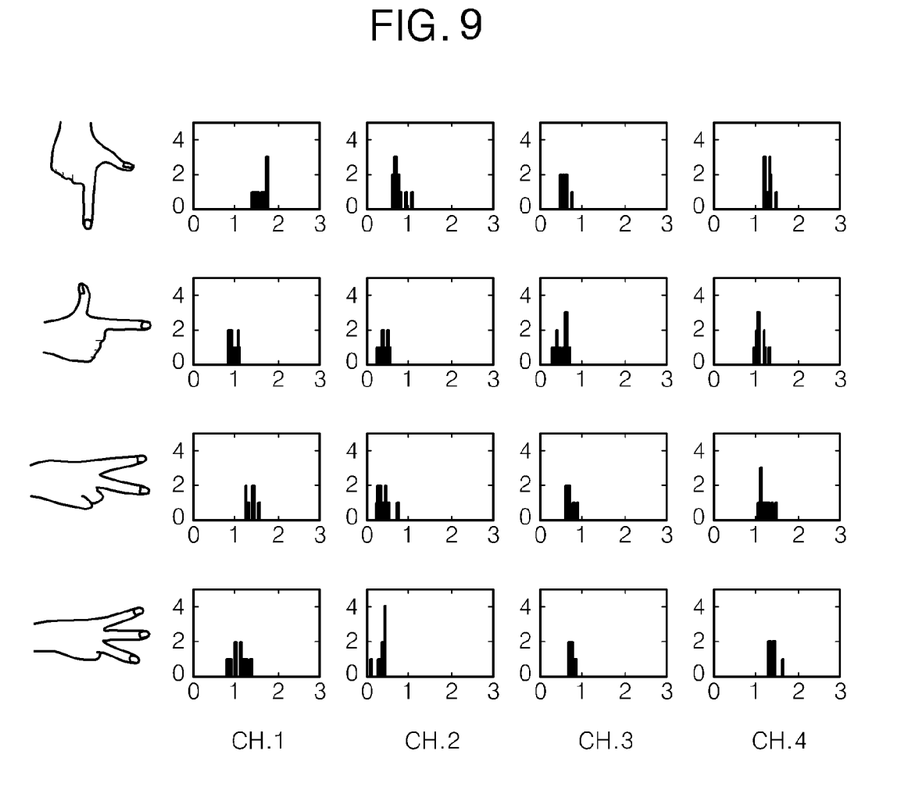
FIG. 9 shows an example of entropy results of electromyogram measurement signals obtained from four channels with respect to each fingerspelling motion in accordance with the present invention.

FIG. 9 shows an example of entropy results of electromyogram measurement signals obtained from four channels with respect to each fingerspelling motion in accordance with the present invention. FIG. 9 shows a histogram constituted of the entropy value obtained from each channel with respect to each motion. The transverse axis indicates the entropy, and the longitudinal axis indicates the number of times of generation.

The Gaussian probability density model of the entropy obtained as described above is obtained by Equation 7.

$$f_{T_c^k}(t_c^k) = \frac{1}{\sqrt{2\Pi\sigma^2}} \exp\left[-\frac{1}{2\sigma^2}(t_c^k - \mu)^2\right] \quad \text{Equation 7}$$

Equation 7 is a general formula of a Gaussian probability density function and corresponds to the Gaussian model. An input $t_c^k$ is the entropy when the motion k is performed at the channel c, $\sigma$ is the standard deviation, and $\mu$ indicates the average. Further, Equation 7 is a basic formula of the Gaussian model, and detailed description thereof will be omitted.

After step S130, the Gaussian model acquired as described above is compared with Gaussian candidate models of candidate fingerspelling motions belonging to the corresponding group, and the candidate fingerspelling motion corresponding to the Gaussian candidate model having highest similarity is recognized as the current fingerspelling motion of the subject (S140). Step S140 is performed by the manual alphabet recognizing part 150.

In step S120 described above, the current gyro signal obtained by the gyro sensor 2 is analyzed. Thereby, it is determined to which of the existing clustered groups the analyzed signal belongs. In step S130, the Gaussian model of the current electromyogram measurement signal obtained by the electromyogram sensor 1 is acquired.

Here, in step S140, the Gaussian model of the electromyogram measurement signal obtained in step S130 is compared with the Gaussian model (Gaussian candidate model) of the electromyogram measurement signals of the candidate fingerspelling motions belonging to the corresponding group determined in step S120, and the candidate fingerspelling motion corresponding to the Gaussian candidate model having highest similarity is recognized as the current motion.

Figure 10:
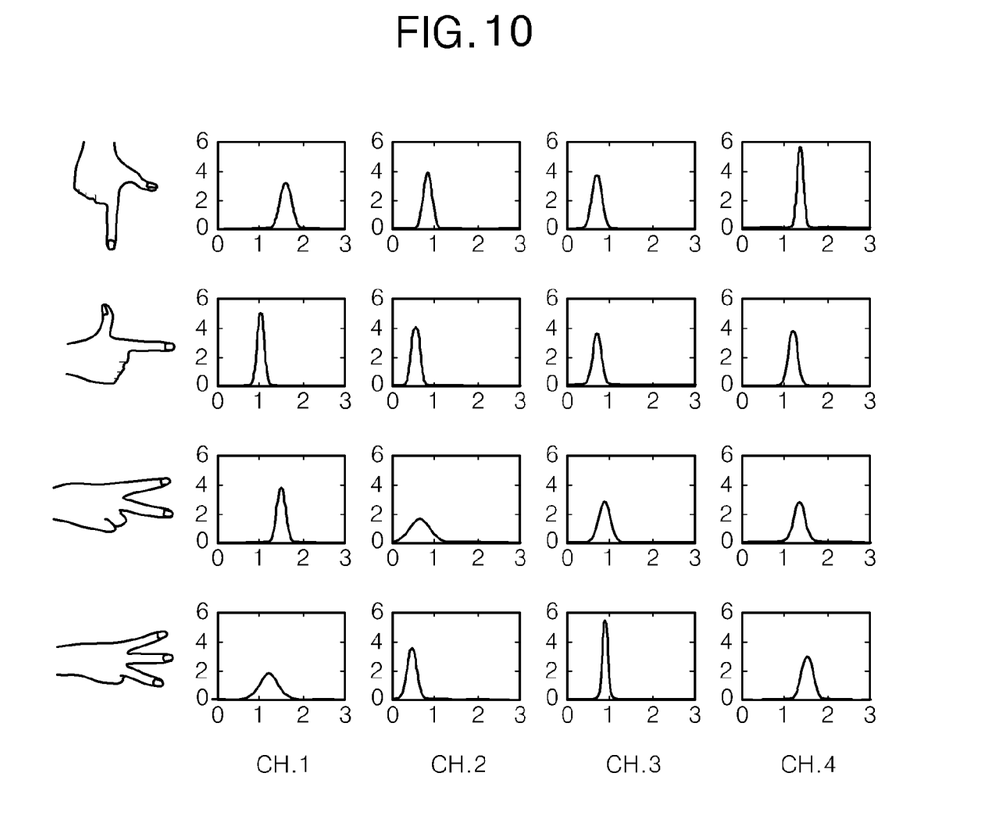
FIG. 10 shows examples of Gaussian models for acquired fingerspelling motions in accordance with the present invention.

It is apparent that for this comparing process, standard Gaussian models of all the fingerspelling motions (in the case of the Korean alphabet, a total of 28 fingerspelling motions) are preferably acquired in advance and are converted into a database. FIG. 10 shows examples of Gaussian models for acquired fingerspelling motions in accordance with an embodiment of the present invention. This is examples of the Gaussian models obtained from the four channels with respect to the four motions. It can be found that different Gaussian models are formed for the respective motions.

In the present embodiment, since the four electromyogram sensors 1 are used, step S140 will be described in greater detail based on these sensors. Individual similarities between the Gaussian models of the electromyogram measurement signals from the four electromyogram sensors 1 and the Gaussian candidate models of the fingerspelling motions belonging to the corresponding group are calculated. For example, when the candidate fingerspelling motions within the corresponding group are four in total, channel-specific similarity values, i.e. four similarity values, of one candidate fingerspelling motion are obtained. When the four candidate fingerspelling motions are considered in total, a total of 16 similarity values are calculated.

Then, the candidate fingerspelling motion in which the product of the calculated individual similarities shows the greatest value is recognized as the current fingerspelling motion. For example, values obtained by multiplying the four similarities calculated from the candidate fingerspelling motion by each other are calculated for each motion. The values are compared for each motion, and the corresponding candidate fingerspelling motion having the greatest value of the product is recognized as the current fingerspelling motion.

This process refers to Equations 8 and 9.

$$L(k) = \Pi_{c=1}^{4} f_{T_c^k}(t_c^k | F_k)$$ Equation 8

Equation 8 uses a maximum likelihood estimation method and refers to a method of obtaining a value of likelihood. That is, a value of the product of the similarities of each fingerspelling motion can be calculated for each channel. If the candidate motions are four, values of L(1) to L(4) should be obtained. A value of k that makes L(1) to L(4) greatest becomes a number of the determined motion.

Describing Equation 8 in detail, $F_k$ indicates the Gaussian model of the k motion, and $t_c^k | F_k$ is a value of information entropy of the electromyogram signal measured through the channel c by the motion of the subject. That is, the function of L(k) is a value obtained by multiplying a value calculated by substituting a value of the generated entropy into the probability density function for each channel.

If a result of inputting the entropy value of a specific channel to the probability density function of the corresponding channel is zero (0), this means that a probability of the electromyogram signal of the channel being obtained from the corresponding motion is almost zero. Since the value of L(k) is obtained by multiplying the value of the probability density function of each channel, if the value of the probability density function is zero even at one channel, the value of L(k) of the corresponding motion becomes zero.

$$\hat{k} = \underset{k}{\operatorname{argmax}} \sum_{c=1}^{4} \log(f_{T_c^k}(t_c^k | F_k))$$ Equation 9

Equation 9 is to estimate the motion $\hat{k}$ that maximizes the value associated with Equation 8, and a log function is used. That is, k that maximizes a value of log L(k) taking a log of the function of L(k) is obtained. This is to apply mathematical knowledge in which multiplication is converted into addition by taking the log. In other words, the motion $\hat{k}$ refers to the fingerspelling motions recognized and determined by the present invention. Thus, an identification number $\hat{k}$ of the motion to be obtained is a value that maximizes the sum of values of log L(k).

Figure 11:
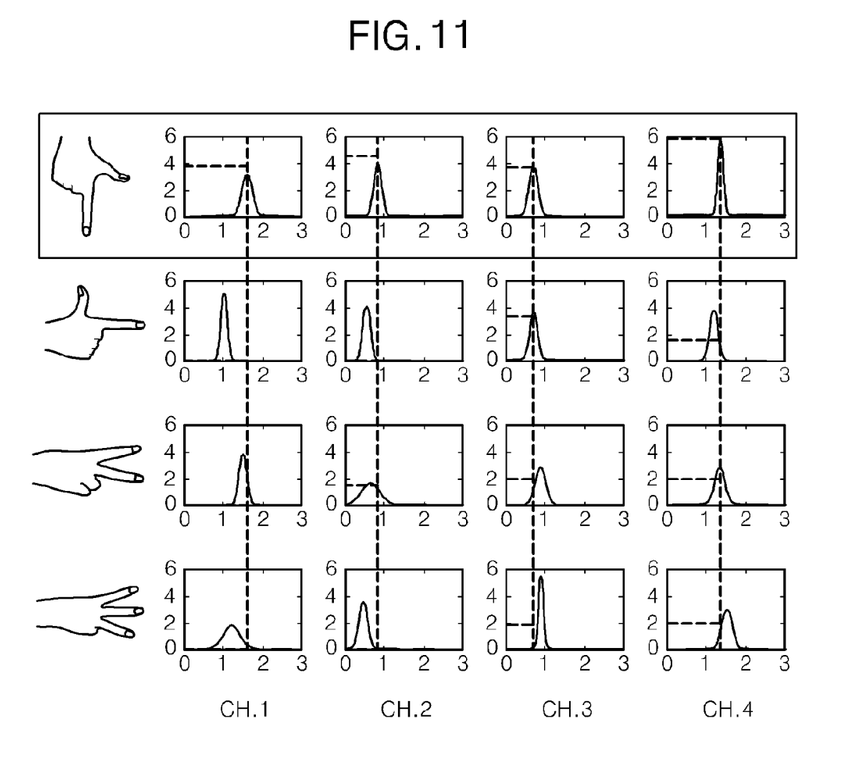
FIG. 11 shows examples of results of recognizing fingerspelling motions in accordance with the present invention.

FIG. 11 shows examples of results of recognizing fingerspelling motions in accordance with an embodiment of the present invention. FIG. 11 shows probability density function (Gaussian model) graphs of the entropies measured from four channels (Ch. 1, Ch. 2, Ch. 3, and Ch. 4) with respect to four motions (motion 1, motion 2, motion 3, and motion 4 in the order from the top to the bottom).

A straight line drawn for each channel in a longitudinal direction shows an entropy value measured for each channel by the motion of the subject. That is, a value of a y axis of a point at which the longitudinal straight line intersects each graph is a value of the probability density function of each channel and motion. As described above, if the value of the probability density function is zero even at one channel with respect to a specific motion k, a probability with which the motion of the subject will be the motion k is close to zero. In case of the channel Ch 2, since values of the motions 2 and 4 are zero, it can be found that the probability with which the motion will be the motions 2 and 4 is next to zero. Consequently, the motion 1 in which a value of the product of the probability density function of each channel is greatest may be determined as the motion of the subject. That is, the motion 1 is detected as a motion that is highest in similarity to the motion of the subject.

Figure 12:
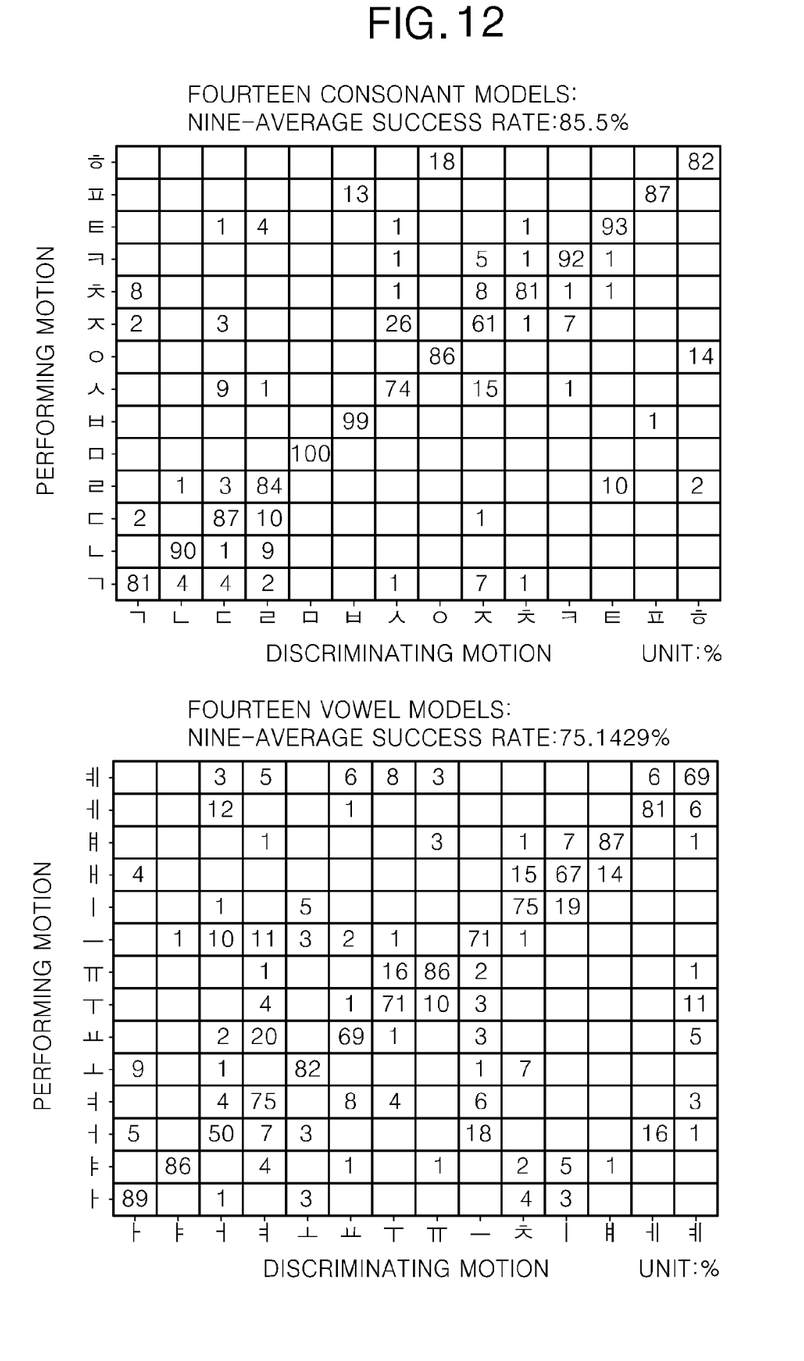
FIG. 12 shows data of a success rate of fingerspelling motion recognition in accordance with the present invention.

FIG. 12 shows data of a success rate of fingerspelling motion recognition in accordance with an embodiment of the present invention. An average success rate of fingerspelling motion recognition of 14 consonants is 85.5%, and an average success rate of fingerspelling motion recognition of 14 vowels is 75.14%. Thus, it can be seen that the results of recognition is reliable.

According to the method and apparatus for recognizing sign language using an electromyogram sensor and a gyro sensor in accordance with the present invention, accuracy and reliability of the recognition of fingerspelling motions can be enhanced using clustering data of the similar fingerspelling motions based on the gyro sensor and Gaussian model data of each fingerspelling motion based on the electromyogram sensor.

The present invention can be implemented as computer readable codes in a computer readable record medium. The computer readable record medium includes all types of record media in which computer readable data are stored. Examples of the computer readable record medium include a ROM, a RAM, a CD-ROM, a magnetic tape, a floppy disk, and an optical data storage. Further, the record medium may be implemented in the form of a carrier wave such as Internet transmission. In addition, the computer readable record medium may be distributed to computer systems over a network, in which computer readable codes may be stored and executed in a distributed manner.

Although an exemplary embodiment of the present invention has been described, those skilled in the art will readily appreciate that the present invention is not limited to the aforementioned specific exemplary embodiment, and many modifications are possible in the embodiments without departing from the gist of the present invention as defined in the claims. Accordingly, all such modifications are intended to be included within the scope of the present invention as defined in the claims.

The invention claimed is:

1. A method for recognizing sign language using at least one electromyogram sensor and at least one gyro sensor, the method comprising:

storing a set of Gaussian candidate models for a plurality of fingerspelling motions;

grouping the set of Gaussian candidate models into predetermined gyro groups;

receiving a first gyro measurement signal from the at least one gyro sensor and a first electromyogram measurement signal from the at least one electromyogram sensor, wherein the at least one gyro sensor and the at least one electromyogram sensor are attached to a body of a subject and wherein the first gyro measurement signal includes a first pitch rotation and a first roll rotation;

determining a first gyro group which is in closest proximity to the first gyro measurement signal among the predetermined gyro groups;

acquiring a first Gaussian model for the first electromyogram measurement signal;

comparing the first Gaussian model with the set of Gaussian candidate models in the first gyro group; determining a first Gaussian candidate model which is in closest proximity to the first Gaussian model, wherein the first Gaussian candidate model is an element of the set of Gaussian candidate models in the first gyro group; and determining a first fingerspelling motion which corresponds to the first Gaussian candidate model.

2. The method according to of claim 1, wherein the grouping further comprises: obtaining a first rotational angle coordinate sample for each of the plurality of fingerspelling motions using roll and pitch rotation values acquired from the at least one gyro sensor;
   measuring a distance from a first central coordinate for each of the predetermined gyro groups with respect to the first rotational angle coordinate sample and assigning the first rotational angle coordinate sample to a group in closest proximity to the first rotational angle coordinate sample;
   calculating a second central coordinate according to an average value of the first rotational angle coordinate sample and the first central coordinate; and
   repeating steps of the measuring and the calculating.

3. The method of claim 1, wherein each of the at least one electromyogram sensor has a different channel from one another, and wherein the acquiring further comprises:
   obtaining an entropy for each of electromyogram measurement signals acquired from the at least one electromyogram sensor; and
   obtaining the first Gaussian model according to the entropy.

4. The method of claim 3, wherein the comparing further comprises:
   calculating individual similarities between the first Gaussian model of each of the electromyogram measurement signals acquired from the at least one electromyogram sensor and the set of Gaussian candidate models in the first group; and
   determining the first Gaussian candidate in which a product of the calculated individual similarities has a greatest value as the first fingerspelling motion of the subject.

5. The method of claim 4, wherein the individual similarities are calculated using a maximum likelihood estimation method.

6. An apparatus for recognizing sign language using at least one electromyogram sensor and at least one gyro sensor, the apparatus comprising:
   a processor configured to store a set of Gaussian candidate models for a plurality of fingerspelling motions and to group the set of Gaussian candidate models into predetermined gyro groups;
   a signal receiving part configured to receive a first gyro measurement signal from at least one gyro sensor and a first electromyogram measurement signal from the at least one electromyogram sensor, wherein the at least one gyro sensor and the at least one electromyogram sensor are attached to a body of a subject, and wherein the first gyro measurement signal includes a first pitch rotation and a first roll rotation;
   a group determining part configured to determine a first gyro group which is in closest proximity to the first gyro measurement signal among the predetermined gyro groups;
   a model acquiring part configured to acquire a first Gaussian model for the first electromyogram measurement signal; and
   a sign language recognizing part configured to compare the first Gaussian model with the set of Gaussian candidate models in the first gyro group, and to recognize a first fingerspelling motion which corresponds to the first Gaussian candidate model.

7. The apparatus of claim 6, wherein the apparatus further comprises a clustering part configured:
   to obtain a first rotational angle coordinate sample for each of the plurality of fingerspelling motions using roll and pitch rotation values acquired from the at least one gyro sensor;
   to measure a distance from a first central coordinate for each of the predetermined gyro groups with respect to the first rotational angle coordinate sample and to assign the first rotational angle coordinate sample to a group in closest proximity to the first rotational angle coordinate sample;
   to calculate a second central coordinate according to an average value of the first rotational angle coordinate sample and the first central coordinate; and
   to repeat the processes of the measuring and the calculating.

8. The apparatus of claim 6, wherein each of the at least one electromyogram sensor has a different channel from one another, and wherein the model acquiring part obtains an entropy for each of electromyogram measurement signals acquired from the at least one electromyogram sensor and acquires the first Gaussian model according to the entropy.

9. The apparatus of claim 8, wherein a manual alphabet recognizing part calculates individual similarities between the first Gaussian model of each of the electromyogram measurement signals acquired from the at least one electromyogram sensor and the set of Gaussian candidate models in the first group and determines the first Gaussian candidate in which a product of the calculated individual similarities has a greatest value as the first fingerspelling motion of the subject.

10. The apparatus of claim 9, wherein the individual similarities are calculated using a maximum likelihood estimation method.

11. A method for recognizing sign language using at least one electromyogram sensor and at least one gyro sensor, the method comprising:
   storing a set of Gaussian candidate models for a plurality of fingerspelling motions;
   grouping the set of Gaussian candidate models into predetermined gyro groups;
   receiving a first gyro measurement signal and a first electromyogram measurement signal from the at least one gyro sensor and the at least one electromyogram sensor;
   determining a first gyro group which is in closest proximity to the first gyro measurement signal among the predetermined gyro groups;
   acquiring a first Gaussian model for the first electromyogram measurement signal;
   comparing the first Gaussian model with the set of Gaussian candidate models in the first gyro group;
   determining a first Gaussian candidate model which is in closest proximity to the first Gaussian model, wherein the first Gaussian candidate model is an element of the set of Gaussian candidate models in the first gyro group; and
   determining a first fingerspelling motion which corresponds to the first Gaussian candidate model, wherein the first gyro measurement signal includes a first pitch rotation $g_p[n]$ and a first roll rotation $g_r[n]$, wherein the first pitch rotation $g_p[n]$ and the first roll rotation $g_r[n]$ satisfy the following equation:

$$g_r[n] = \sum_{t=1}^{\infty} \int_0^{0.1} V_r[n]\,dn,\ g_p[n] = \sum_{t=1}^{\infty} \int_0^{0.1} V_p[n]\,dn,$$

and
   wherein $V_r[n]$ denotes an angular velocity of the first roll rotation gr[n] and $V_P[n]$ denotes an angular velocity of the first pitch rotation $g_p[n]$.

12. The method of claim 11, wherein the acquiring the first Gaussian model is obtained in accordance with the following equation:

$$f_{T_c^k}(t_c^k) = \frac{1}{\sqrt{2\Pi\sigma^2}} \exp\left[-\frac{1}{2\sigma^2}(t_c^k - \mu)^2\right],$$

wherein $t_c^k$ denotes an entropy, a motion k is performed at a channel c, δ denotes a standard deviation, and μ denotes an average,
wherein the entropy of a signal x is calculated by the following equation $$H(X) = -\Sigma_{m=1}^{M} p(X_m) \log p(X_m),$$

$$P_c^k(m) = \frac{\text{number of samples} \in I_m}{\text{number of total samples}}, \text{ and}$$

$$I_m = \left\{ x_c^k[\cdot] \Big| \frac{(m-1)}{M} x_{max} \le x_c^k[\cdot] < \frac{m}{M} x_{max} \right\},$$

wherein $p_c^k(m)$ denotes a probability at which the signal sample is present in a section $I_M$ and $x_c^k$ is calculated by the following equation: $x_c^k = |r_c^k[n]|$ and wherein $r_c^k[n]$ denotes a raw signal, and $x_c^k[n]$ denotes an absolute value of the raw signal, k denotes an arbitrary fingerspelling motion, and c denotes a channel of the at least one electromyogram sensor.

13. The method of claim 11, wherein the grouping into the predetermined gyro groups further comprises grouping by an orientation of each of the fingerspelling motions.

14. The method of claim 13, wherein the orientation of each of the fingerspelling motions includes fingers oriented downward, fingers parallel with a ground, and fingers oriented upward.

* * * * *